United States Patent
Wilkinson et al.

(10) Patent No.: US 7,422,573 B2
(45) Date of Patent: Sep. 9, 2008

(54) FORWARD BLUNTING WINGSET WITH LEAF SPRING DRIVEN SHIELD

(75) Inventors: Bradley Wilkinson, North Haledon, NJ (US); C. Mark Newby, Tuxedo, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 900 days.

(21) Appl. No.: 10/736,213

(22) Filed: Dec. 15, 2003

(65) Prior Publication Data

US 2004/0167477 A1 Aug. 26, 2004

Related U.S. Application Data

(60) Provisional application No. 60/435,634, filed on Dec. 19, 2002.

(51) Int. Cl.
*A61M 5/00* (2006.01)
(52) U.S. Cl. .................. 604/263; 604/177
(58) Field of Classification Search ........... 604/164.01, 604/164.08, 165.03, 174, 177, 263.187, 197, 604/198, 110; 128/919; 600/576
See application file for complete search history.

(56) References Cited

U.S. PATENT DOCUMENTS

| | | | |
|---|---|---|---|
| 2,725,058 A | 11/1955 | Rathkey | |
| 4,139,009 A | 2/1979 | Alvarez | |
| 4,735,618 A | 4/1988 | Hagen | |
| 4,867,746 A | 9/1989 | Dufresne | |
| 4,892,521 A | 1/1990 | Laico et al. | |
| 4,909,794 A | 3/1990 | Haber et al. | |
| 4,911,706 A | 3/1990 | Levitt | |
| 4,998,922 A | 3/1991 | Kuracina et al. | |
| 5,051,109 A | 9/1991 | Simon | |
| 5,059,184 A | 10/1991 | Dyke | |
| 5,067,946 A * | 11/1991 | Zhadanov | 604/198 |
| 5,108,376 A * | 4/1992 | Bonaldo | 604/171 |
| 5,152,751 A | 10/1992 | Kozlowski | |
| 5,176,655 A | 1/1993 | McCormick et al. | |
| 5,242,418 A | 9/1993 | Weinstein | |
| 5,250,031 A | 10/1993 | Kaplan et al. | |
| 5,256,152 A | 10/1993 | Marks | |
| 5,295,972 A | 3/1994 | Mischenko | |

(Continued)

FOREIGN PATENT DOCUMENTS

EP 1 132 103 A1 9/2001

(Continued)

*Primary Examiner*—Nicholas D. Lucchesi
*Assistant Examiner*—Aarti Bhatia
(74) *Attorney, Agent, or Firm*—Mark J. Schildkraut

(57) ABSTRACT

A shieldable needle device is provided. The shieldable needle device includes a housing, a needle cannula, a tip guard and a flexibly resilient drive mechanism. The housing includes a first lateral extension and a second lateral extension which are interconnected at a rearward end to form a hub portion from which the needle cannula extends. The tip guard telescopes over the needle cannula from a retracted position to an extended position. The drive mechanism is attached to the tip guard and is bent or coiled within the housing between the first and second lateral extension and retained in the bent or coiled position. Upon release of the drive mechanism, the tip guard is moved from a retracted position to an extended position, thereby protectively surrounding a tip of the needle cannula.

20 Claims, 12 Drawing Sheets

U.S. PATENT DOCUMENTS

| | | | |
|---|---|---|---|
| 5,312,372 A | | 5/1994 | DeHarde et al. |
| 5,334,158 A | | 8/1994 | McLees |
| 5,348,544 A | * | 9/1994 | Sweeney et al. ............ 604/192 |
| 5,423,766 A | | 6/1995 | DiCesare |
| 5,425,720 A | | 6/1995 | Rogalsky et al. |
| 5,538,508 A | | 7/1996 | Steyn |
| 5,549,570 A | | 8/1996 | Rogalsky |
| 5,558,651 A | * | 9/1996 | Crawford et al. ............ 604/263 |
| 5,569,202 A | | 10/1996 | Kovalic et al. |
| 5,584,818 A | | 12/1996 | Morrison |
| 5,676,658 A | | 10/1997 | Erskine |
| 5,746,215 A | * | 5/1998 | Manjarrez ................... 600/573 |
| 5,746,718 A | | 5/1998 | Steyn |
| 5,779,679 A | * | 7/1998 | Shaw .......................... 604/158 |
| 5,810,784 A | | 9/1998 | Tamaro |
| 5,910,132 A | | 6/1999 | Schultz |
| 5,919,168 A | | 7/1999 | Wheeler |
| 5,925,020 A | | 7/1999 | Nestell |
| 5,951,522 A | | 9/1999 | Rosato et al. |
| 5,951,525 A | * | 9/1999 | Thorne et al. ............... 604/198 |
| 6,210,371 B1 | | 4/2001 | Shaw |
| 6,287,278 B1 | | 9/2001 | Woehr et al. |
| 6,537,259 B1 | * | 3/2003 | Niermann ................... 604/263 |
| 6,835,190 B2 | * | 12/2004 | Nguyen ....................... 604/198 |
| 6,926,700 B2 | * | 8/2005 | Bressler et al. ............. 604/263 |
| 6,932,803 B2 | * | 8/2005 | Newby ........................ 604/500 |
| 7,018,344 B2 | * | 3/2006 | Bressler et al. ............. 600/573 |
| 7,041,066 B2 | * | 5/2006 | Wilkinson ................... 600/576 |
| 7,144,388 B2 | * | 12/2006 | Crawford .................... 604/192 |
| 7,150,725 B2 | * | 12/2006 | Wilkinson ................... 604/162 |
| 2002/0065488 A1 | | 5/2002 | Suzuki et al. |
| 2002/0120215 A1 | * | 8/2002 | Crawford et al. ............ 600/573 |
| 2003/0181869 A1 | * | 9/2003 | Swenson et al. ............ 604/263 |
| 2003/0181870 A1 | * | 9/2003 | Bressler et al. ............. 604/263 |
| 2003/0181871 A1 | * | 9/2003 | Wilkinson et al. .......... 604/263 |
| 2003/0181872 A1 | * | 9/2003 | Newby ........................ 604/263 |
| 2007/0100296 A1 | * | 5/2007 | Hwang ........................ 604/263 |

FOREIGN PATENT DOCUMENTS

| | | |
|---|---|---|
| EP | 1 350 537 A1 | 10/2003 |
| EP | 1 362 608 A2 | 11/2003 |

* cited by examiner

FORWARD BLUNTING WINGSET WITH LEAF SPRING DRIVEN SHIELD

CROSS-REFERENCE TO RELATED APPLICATION

This application claims priority to U.S. Provisional Patent Application No. 60/435,634 filed Dec. 19, 2002.

BACKGROUND OF THE INVENTION

1. Field of the Invention

The present invention relates to safety needle devices for safe and convenient handling of needles. More particularly, the present invention relates to a shieldable needle device having a forward moving safety shield for protection from a used needle tip.

2. Description of Related Art

Disposable medical devices having medical needles are used for administering medication or withdrawing fluid from the body of a patient. Such disposable medical devices typically include blood-collecting needles, fluid handling needles and assemblies thereof. Current medical practice requires that fluid containers and needle assemblies used in such devices be inexpensive and readily disposable. Consequently, existing blood collection devices typically employ some form of durable, reusable holder on which detachable and disposable medical needles and fluid collection tubes may be mounted. A blood collection device of this nature may be assembled prior to use and then disassembled after use. Thus, these blood collection devices allow repeated use of a relatively expensive holder upon replacement of relatively inexpensive medical needles and/or fluid collection tubes. In addition to reducing the cost of collecting blood specimens, these blood collection devices help minimize the production of hazardous waste material.

A blood collection device or intravenous (IV) infusion device typically includes a needle cannula having a proximal end, a pointed distal end, and a lumen extending therebetween. The proximal end of the needle cannula is securely mounted in a plastic hub defining a central passage that communicates with the lumen extending through the needle cannula. A thin, flexible thermoplastic tube is connected to the hub and communicates with the lumen of the needle cannula. The end of the plastic tube remote from the needle cannula may include a fixture for connecting the needle cannula to a blood collection tube or other receptacle. The specific construction of the fixture will depend upon the characteristics of the receptacle to which the fixture is to be connected.

In order to reduce the risk of incurring an accidental needle-stick wound, protection of used needle cannulas becomes important. With concern about infection and transmission of diseases, methods and devices to enclose or cover the used needle cannula have become very important and in great demand in the medical field. For example, needle assemblies commonly employ a safety shield that can be moved into shielding engagement with a used needle cannula to minimize risk of an accidental needle stick.

For example, U.S. Pat. No. 4,892,521 to Laico et al. discloses a telescoping protective cover, which utilizes a pair of guide members to extend a telescoping tip guard to a shielding position. The guide members are diametrically located and function to guide the tip guard to the protective position and may be spring biased.

U.S. Pat. No. 5,423,766 to DiCesare discloses a safety shield including a tip guard that is slideably movable along the needle from a proximal position to a distal position. The safety shield utilizes a spring tether which is connected to a guard and an anchor. The tether is deflected into a loop with the guard and anchor preventing the tether from springing open.

Such prior art devices are typically difficult to manufacture and require complex operation to operate. In view of the foregoing, a need exists for a blood collection set including a shieldable needle device that achieves secure and effective shielding of a used needle cannula, which is easy to manufacture and is simple and safe to operate.

SUMMARY OF THE INVENTION

The present invention is directed to a shieldable needle device including a housing, a needle cannula, a tip guard and a flexibly resilient drive mechanism. The housing includes a first lateral extension and a second lateral extension which are interconnected at a rearward end to form a hub portion. The needle cannula includes a forward end and a rearward end, and extends from the hub portion of the housing. The tip guard is axially movable along the needle cannula between a retracted position where the forward end of the needle cannula is exposed and an extended position where the tip guard protectively surrounds the forward end of the needle cannula. The drive mechanism is provided for biasing the tip guard to the extended position, and includes a first end anchored to the housing between the first lateral extension and the second lateral extension, and a second end anchored to the tip guard. The drive mechanism is capable of being retained in a biased state between the first lateral extension and the second lateral extension when the tip guard is in the retracted position. Preferably, the drive mechanism is a leaf spring, or a coiled spring wound between the first lateral extension and the second lateral extension.

The drive mechanism preferably includes a mechanism, such as a locking lug, which is capable of frictional or abutting engagement with the housing for retaining the drive mechanism in a biased state between the first lateral extension and the second lateral extension when the tip guard is in the retracted position. In addition, a release latch may be provided for releasing the locking lug from engagement with the housing, thereby causing the drive mechanism to release energy and bias the tip guard to the extended position.

In particularly preferred embodiments, the first lateral extension of the housing includes a first lateral wing and the second lateral extension of the housing includes a second lateral wing, with the first and second lateral wings forming a pair of generally planar wings extending from opposing sides of the housing to form a wingset, which is particularly adapted for connection to a blood collection set.

Thus, in one particular embodiment, the present invention is directed to a shieldable needle wingset for blood collection, which includes a needle device as described above, and also includes a fixture for connecting the wingset to a receptacle, and a flexible tube connected between the fixture and the wingset.

DETAILED DESCRIPTION

Figure 1:
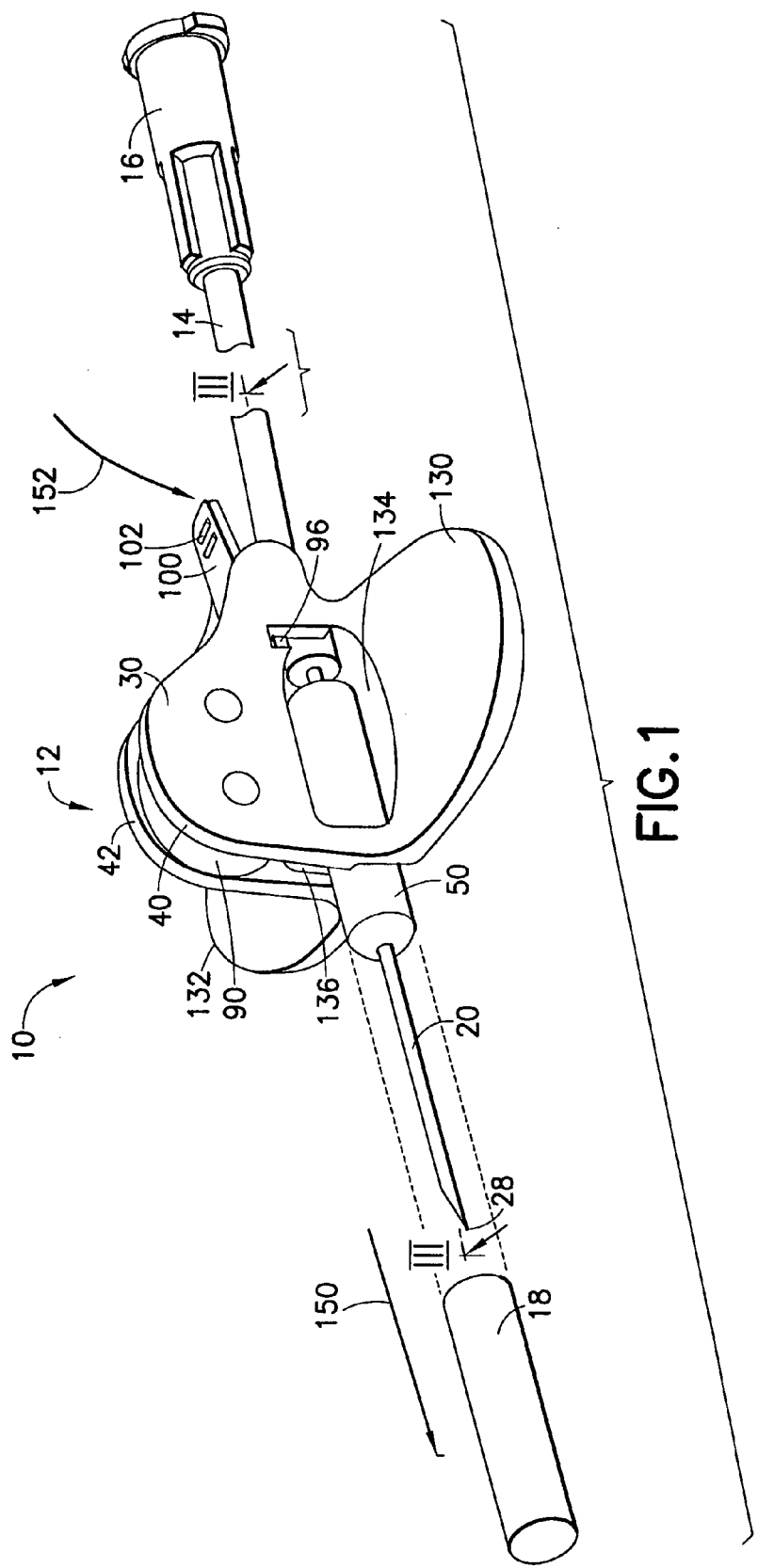
FIG. 1 is a perspective view of a blood collection set including a shieldable needle device, in accordance with the present invention, shown in a retracted or sampling state.

Referring to the drawings in which like reference characters refer to like parts throughout the several views thereof, FIG. 1 illustrates a blood collection set in the form of a wingset including a shieldable needle device, in accordance with the present invention and the related features. The present invention is generally described in terms of a shieldable needle device. FIG. 1 illustrates the shieldable needle device in the form of a blood collection set 10 including a shieldable needle device 12. While described herein in terms of one embodiment of a blood collection set, the shieldable needle device of the present invention may be used with or incorporate other medical devices used in connection with a needle, such as a hypodermic syringe assembly, a hypodermic needle, a double-ended needle assembly for blood collection, an intravenous infusion set, or other handling devices or medical device assemblies that contain piercing elements.

As shown in FIG. 1, blood collection set 10 includes a shieldable needle device 12, a flexible tube 14 extending from needle device 12, a fixture 16 mounted to tube 14, and a packaging cover 18 removably mounted to portions of needle device 12 opposite tube 14, such as through frictional engagement. Shieldable needle device 12 of blood collection set 10 is shown in detail in FIGS. 2 and 3 and includes a needle cannula 20, a housing 30, a tip guard assembly 50 and a flexibly resilient drive mechanism 90.

Needle cannula 20 includes a rearward end or proximal end 22 and a forward end or opposing distal end 24, with lumen 26 extending through needle cannula 20 from proximal end 22 to distal end 24. Distal end 24 of needle cannula 20 is beveled to define a sharp puncture tip 28, such as an intravenous puncture tip. Puncture tip 28 is provided for insertion into a patient's blood vessel, such as a vein, and is therefore designed to provide ease of insertion and minimal discomfort during venipuncture.

Figure 3:
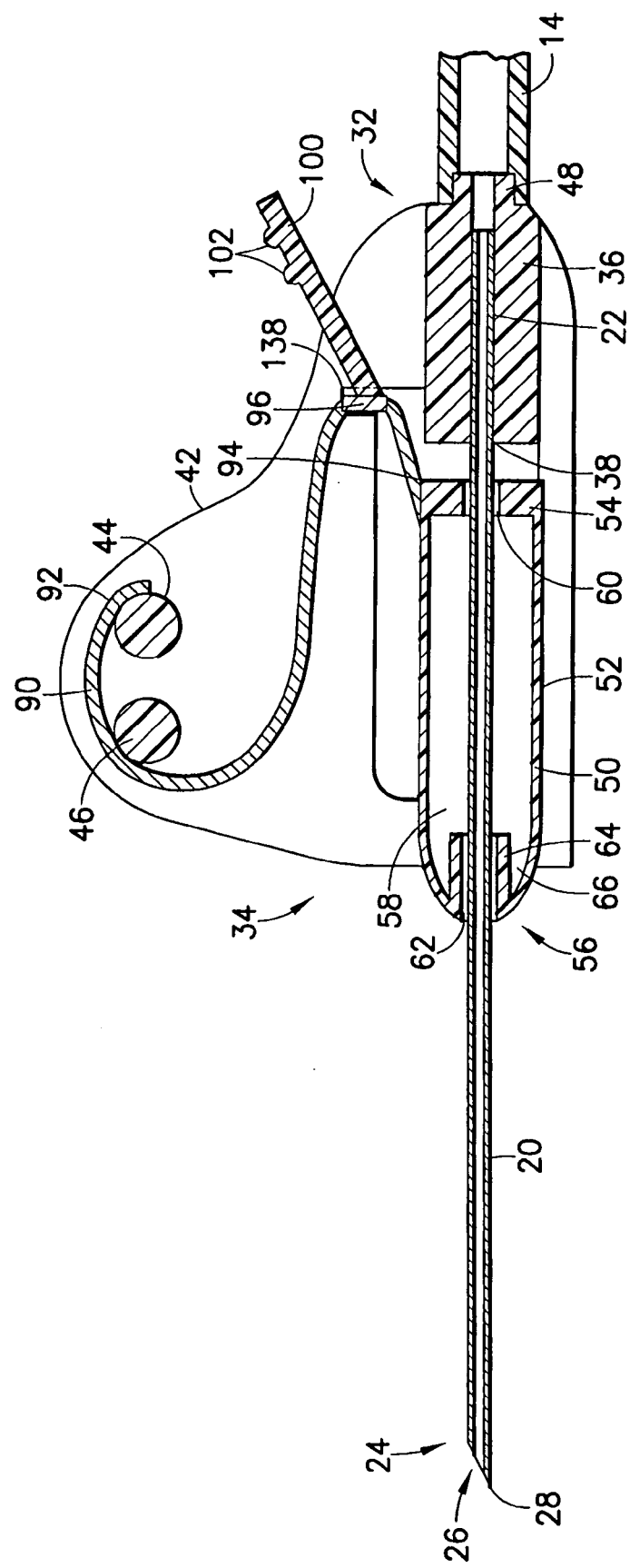
FIG. 3 is a cross-sectional view taken along line III-III of FIG. 1 with the needle device in a sampling state.
Figure 4:
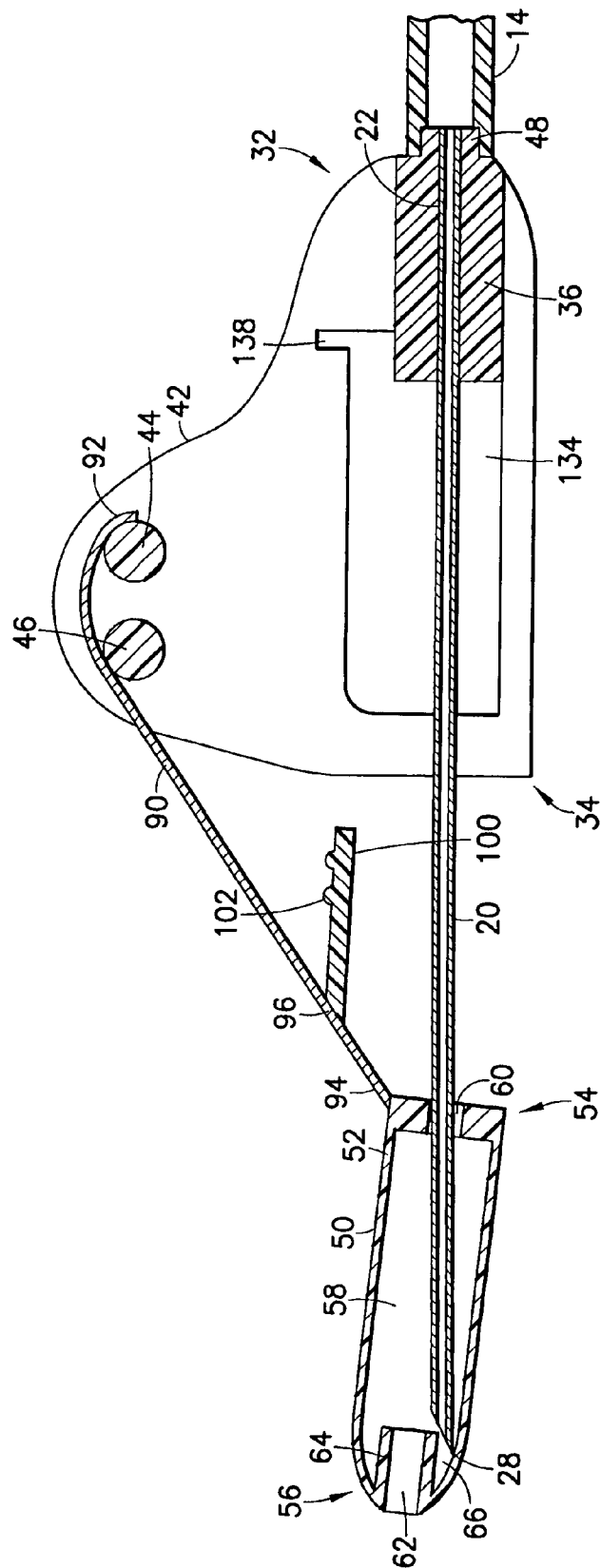
FIG. 4 is a cross-sectional view taken along line IV-IV of FIG. 2 with the needle device in a fully shielded state.

Needle device 12 further includes housing 30. Housing 30 is a unitary structure, desirably molded from a thermoplastic material. Housing 30 generally includes a rearward end or proximal end 32, and an opposing forward end or distal end 34. A hub 36 is providing at proximal end 32 of housing 30, with an internal passageway 38 extending therethrough. Hub 36 is desirably a generally tubular-shaped structure. First lateral extension 40 and second lateral extension 42 extend from opposing lateral sides of hub 36, generally in an upward manner, toward distal end 34 of housing 30, thereby forming a dorsal fin-shaped structure. First lateral extension 40 and second lateral extension 42 are spaced from each other, and are preferably planar structures that are parallelly-spaced. Further, first lateral extension 40 and second lateral extension 42 are interconnected to each other through a connector 44, which is located within the dorsal fin-shaped structure of the lateral extensions. An additional connector 46 may also be provided, as shown in FIGS. 3 and 4, which provides additional structural integrity and provides for mounting of the drive mechanism, which will be discussed in more detail herein.

Housing 30 may further include a first lateral wing 130 extending from the first lateral extension 40, and a second lateral wing 132 extending from the second lateral extension 42. Desirably, first lateral wing 130 and second lateral wing 132 extend from first lateral extension 40 and second lateral extension 42, respectively, at an angle of about 90°. First lateral wing 130 and second lateral wing 132 provide housing 30 and needle device 12 as a butterfly-type wingset assembly with a pair of generally planar wings extending from opposing sides for assisting in positioning and placement of needle device and blood collection set 10 during blood collection procedures. The bottom surface of housing 30 defined by first lateral wing 130 and second lateral wing 132 is generally planar or flat, which provides an effective surface to lie against the skin of a patient during use. First cutaway portion 134 may be provided between first lateral wing 130 and first lateral extension 40, and second cutaway portion 136 may be provided between second lateral wing 132 and second lateral extension 42.

Needle cannula 20 is positioned within internal passageway 38 of hub 36 of housing 30, and extends from forward end 34 of housing 30. Desirably, needle cannula 20 and housing 30 are separate parts which are fixedly attached and secured through an appropriate medical grade adhesive or the like. Housing 30 may further include a nub 48 extending from the rearward or proximal end 32 for attachment with flexible tube 14.

Needle device 12 further includes tip guard assembly 50, which is movable along needle cannula 20 between a first rearward or retracted position adjacent housing 30, and a second forward or extended position adjacent puncture tip 28, as will be described in more detail herein. The tip guard assembly 50 may be any assembly capable of telescoping along needle cannula 20 to a position shielding the tip of the needle. For example, the tip guard assembly 50 may be of a unitary, one-piece construction, or may be of a two-piece construction. Tip guard assembly 50 includes a housing 52, which is a unitary structure, desirably molded from a thermoplastic material, including a rearward or proximal end 54, a forward or distal end 56, and an internal passage 58 extending between a proximal opening 60 and a distal opening 62. Distal end 56 includes an annular wall 64 extending within internal passage 58 from proximal end 54. Annular wall 64 creates a distal pocket 66 extending annularly around annular wall 64 at distal end 56.

In a retracted position, tip guard assembly 50 is positioned along needle cannula 20 between first lateral extension 40 and second lateral extension 42 of housing 30 adjacent distal end 34. Proximal end 54 of tip guard assembly 50 may abut hub 36 of housing 30, or may be spaced therefrom.

Housing 30 and tip guard assembly 50 are interconnected through drive mechanism 90. Drive mechanism 90 provides for activation of the safety shielding feature of shieldable needle device 12 through axial movement of tip guard assembly 50 along needle cannula 20 from the retracted position within housing 30 to an extended position adjacent puncture tip 28, as will be described in more detail herein.

Drive mechanism 90 is an elongated flexibly resilient structure. As employed herein, "flexibly resilient" refers to a structure which is able to bend easily, and which is able to easily resume its original shape after bending. Drive mechanism 90 may be constructed of any material capable of providing such properties, and is desirably constructed of a polymeric or metallic material. Moreover, drive mechanism 90 may include any profile, such as a round, wire-like profile, or a ribbon-like profile. Preferably, drive mechanism 90 is a leaf spring, which is in a biased state when retained in a bent position and automatically resumes its original shape when released.

Drive mechanism 90 includes a first end 92 and a second end 94. First end 92 is anchored to housing 30, such as through an attachment with connector 44 between first lateral extension 40 and second lateral extension 42 at a point between the dorsal fin-shaped structure. Such an attachment may be provided through an appropriate medical grade adhesive or the like. Drive mechanism 90 extends from first end 92 to second end 94 at a location between first lateral extension 40 and second lateral extension 42. When tip guard assembly 50 is in the retracted position with the puncture tip 28 of needle cannula 20 exposed, as shown in FIG. 3, drive mechanism 90 extends from the first end 92 attached to connector 44 in a direction toward distal end 34 of housing 30, and is bent rearwardly toward proximal end 32 of housing 30, such as around a second connector 46. Such bent structure provides drive mechanism 90 with a biasing force, due to the flexible resilient nature of drive mechanism 90. The second end 94 of drive mechanism 90 is attached to tip guard assembly 50, desirably at proximal end 54 thereof. Drive mechanism 90 is of a sufficient length to fully extend when tip guard assembly 50 is in an extended position encompassing the distal end 24 of needle cannula 20.

Figure 2:
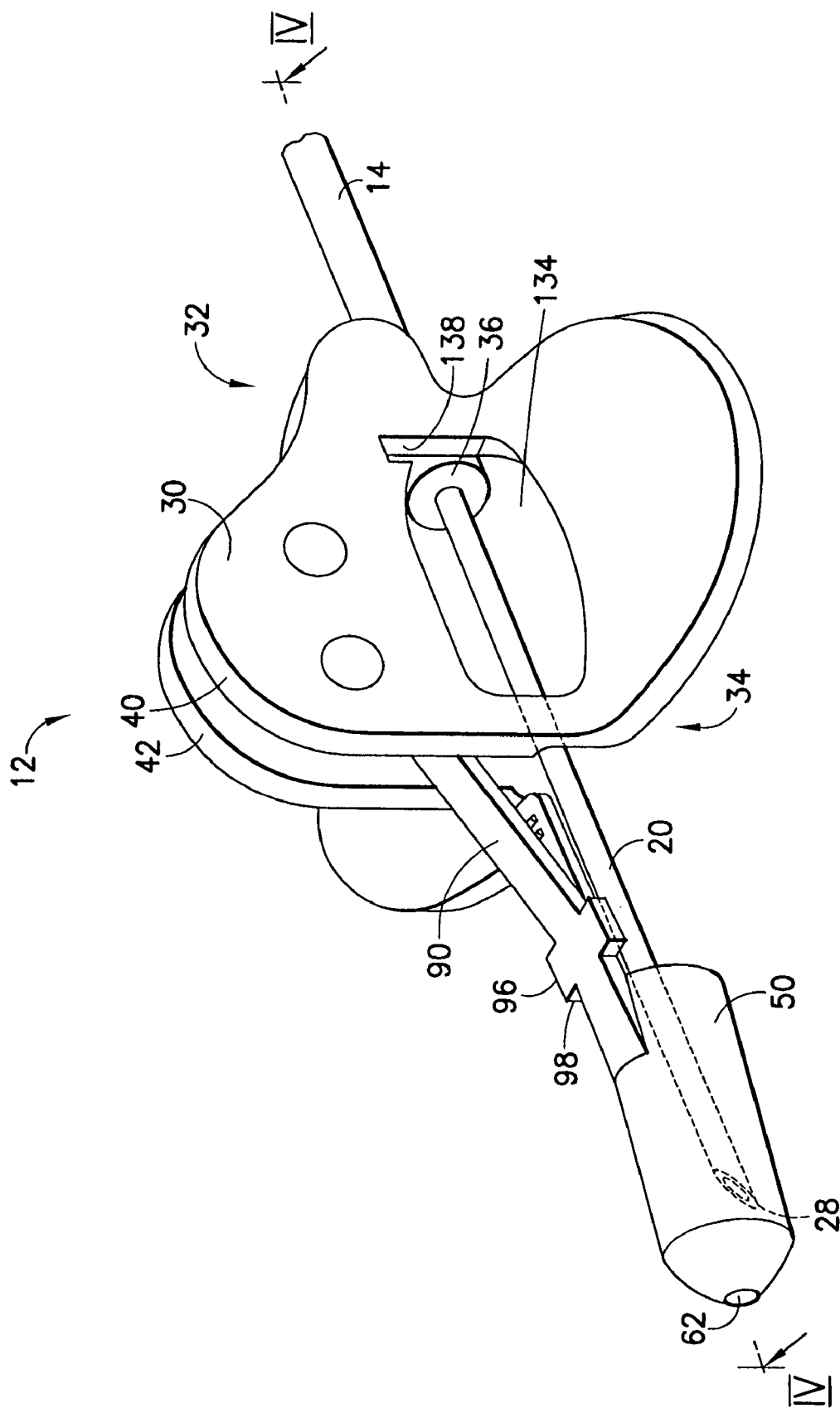
FIG. 2 is a perspective view of the needle device of FIG. 1 shown in a fully shielded state.

Drive mechanism 90 further includes a mechanism for retaining drive mechanism 90 in a biased state between first lateral extension 40 and second lateral extension 42 when tip guard assembly 50 is in the retracted position. For example, as seen in FIG. 2, a lockout lug 96 is desirably provided adjacent second end 94 of drive mechanism 90. Lockout lug 96 includes an edge portion 98 which provides for abutting engagement with a portion of housing 30 for retaining drive mechanism 90 in a biased state, such as in a bent or coiled state, when tip guard assembly 50 is in the retracted position.

More particularly, as noted above, housing 30 may include first cutaway portion 134 and second cutaway portion 136, providing between first lateral wing 130 and first lateral extension 40 and second lateral wing 132 and second lateral extension 42, respectively. One or both of first cutaway portion 134 and second cutaway portion 136 may include profile for frictional engagement with lockout lug 96, such as a notch 138, as shown in FIGS. 2 and 3. Edge portion 98 of lockout lug 96 abuts the edge surface of notch 138, thereby maintaining drive mechanism 90 in a biased state. First and second cutaway portions 134, 136 further provide a means for lockout lug 96 to pass through housing 30 when tip guard assembly 50 is propelled from the retracted position to the extended position through the biasing force of drive mechanism 90, as will be discussed in more detail herein. Alternatively, housing 30 may include interior passages or channels on opposing internal surfaces thereof, acting in a similar manner as first and second cutaway portions 134, 136 for permitting lockout lug 96 to pass through housing 30 during such movement.

Second end 94 of drive mechanism 90 may further include a release latch 100, for releasing lockout lug 96 from abutting engagement with notch 138. Release latch 100 may be an extension portion which is integrally formed with or separately attached to drive mechanism 90. Alternatively, release latch 100 may extend from tip guard assembly 50 as a portion which is integrally formed therewith or separately attached thereto. With such an arrangement, second end 94 of drive mechanism 90 may be attached to release latch 100, providing for ease of release of locking lug 96 from notch 138. Release latch 100 desirably includes a surface having a profile for accommodating a user's finger, such as ribs or bumps 102.

Blood collection set 10 can be packaged substantially in the condition shown in FIG. 1, with drive mechanism 90 in a biased state. Prior to use, blood collection set 10 is removed from its package. Fixture 16 may then be connected to an appropriate receptacle for providing fluid communication with lumen 26 through needle cannula 20.

In use, blood collection set 10 is provided with needle device 12 assembled and including flexible tube 14 extending from needle device 12 and connected to fixture 16. After removing blood collection set 10 from its package, it can be assembled with other appropriate medical equipment for use. For example, a non-patient needle assembly and a needle holder may be connected to blood collection set 10 through fixture 16.

To prepare for use of blood collection set 10, the user grasps blood collection set 10 at needle device 12, with first lateral extension 40 and second lateral entension 42 acting as a surface for grasping between a user's finger and thumb. Packaging cover 18 is then grasped and urged distally in a direction of arrow 150 to disengage from needle cannula 20, thereby exposing puncture tip 28 of needle cannula 20.

The medical practitioner can then urge puncture tip 28 at distal end 24 of needle cannula 20 into a targeted blood vessel of a patient. First and second lateral wings 130, 132 are maintained flush against the patient's skin during such procedure, thereby ensuring that needle device 12 is inserted in the proper orientation within the vessel.

After the targeted blood vessel has been accessed, an appropriate medical procedure can then be conducted. Upon completion of the procedure, such as when all desired samples have been drawn, needle cannula 20 is withdrawn from the patient, and activation of the safety feature of needle device 12 can be accomplished.

To activate the safety feature, release latch 100 is activated by exerting downward pressure in a direction of arrow 152. Such force causes lockout lug 96 to become disengaged from notch 138, thereby eliminating the abutting relationship of edge portion 98 of lockout lug 96 within notch 138. Prior to being released, drive mechanism 90 is bent as shown in FIG. 3, and is therefore in a biased state. After release of lockout lug 96 from notch 138, drive mechanism 90 is free to exert a biasing force. Such release of drive mechanism 90 from its retained position causes it to unbend due to the flexibly resilient nature of drive mechanism 90. Since second end 94 of drive mechanism 90 is fixedly attached to tip guard assembly 50, and since tip guard assembly 50 is axially movable along needle cannula 20, such movement and unbending creates a biasing force between drive mechanism 90 and tip guard assembly 50, which causes tip guard assembly 50 to axially move away from housing 30 toward distal end 24 of needle cannula 20 such that it slides or glides along needle cannula 20 toward distal end 24 due to the biasing force of drive mechanism 90. During such movement, lockout lug 96 passes through housing 30 at first cutaway portion 134 and second cutaway portion 136.

After tip guard assembly 50 is moved along needle cannula 20 to the distal end 24, puncture tip 28 of needle cannula 20 passes entirely through the distal opening 62 within distal end 56 and into the internal passage 58. The biasing force of drive mechanism 90 causes tip guard assembly 50 to then be slightly offset from its longitudinal axis, thereby causing puncture tip 28 to be trapped within distal pocket 66 between housing 52 and annular wall 64, as shown in FIG. 4 Thus, a return movement of tip guard assembly 50 is prevented. Furthermore, drive mechanism 90 has a length that will prevent movement of tip guard assembly 50 distally beyond needle cannula 20. Hence, puncture tip 28 of needle cannula 20 is safely shielded. Blood collection set 10 may then be appropriately discarded.

It is noted that activation of the safety feature may be accomplished while venipuncture is maintained, that is while puncture tip 28 of needle cannula 20 is maintained within the blood vessel of the patient. For example, release latch 100 can be activated while puncture tip 28 is within the patient's blood vessel, thereby axially moving tip guard assembly 50 axially along needle cannula 20. Since puncture tip 28 is within the patient's blood vessel, such distal movement of tip guard assembly 50 will terminate when housing 52 of tip guard assembly 50 contacts the skin of the patient near the puncture site. Upon removal of puncture tip 28 from the patient's blood vessel, tip guard assembly 50 will continue in its axial movement toward the distal end 24 of needle cannula 20 due to the bias exerted through drive mechanism 90. Such axial movement results in tip guard assembly 50 shielding puncture tip 28 of needle cannula 20.

FIGS. 5-14 depict further embodiments of the present invention that include many components which are substantially identical to the components of FIGS. 1-4. Accordingly, similar components performing similar functions will be numbered identically to those components of FIGS. 1-4, except that a suffix "a" will be used to identify those similar components in FIGS. 5 and 6, a suffix "b" will be used to identify those similar components in FIGS. 7 and 8, a suffix "c" will be used to identify those similar components in FIGS. 9 and 10, a suffix "d" will be used to identify those similar components in FIGS. 11 and 12, and a suffix "e" will be used to identify those similar components in FIGS. 13 and 14.

Figure 5:
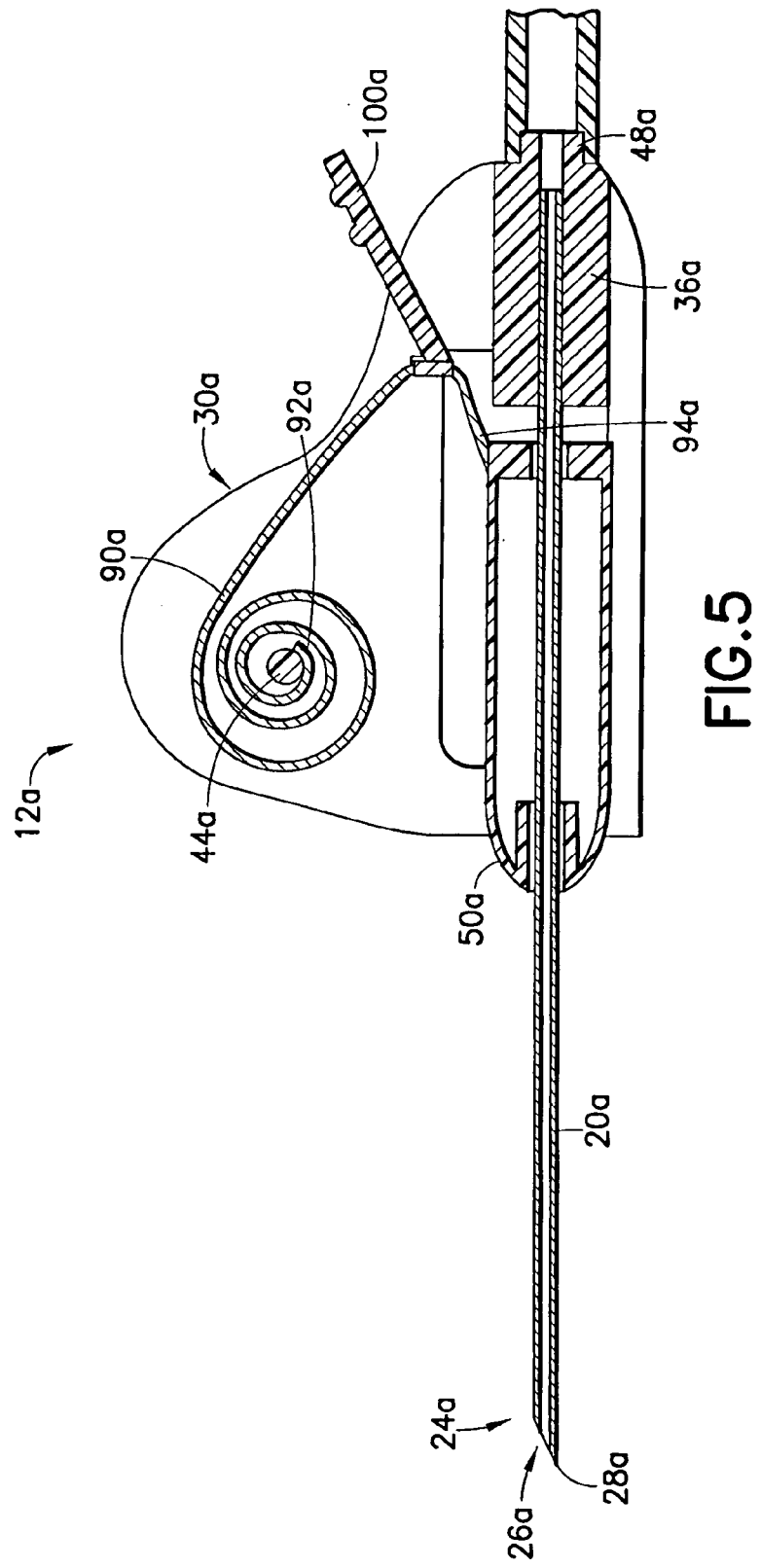
FIG. 5 is a side cross-sectional view of a shieldable needle device in an alternate embodiment of the present invention with a wound coil spring, with the needle device in a sampling state.
Figure 6:
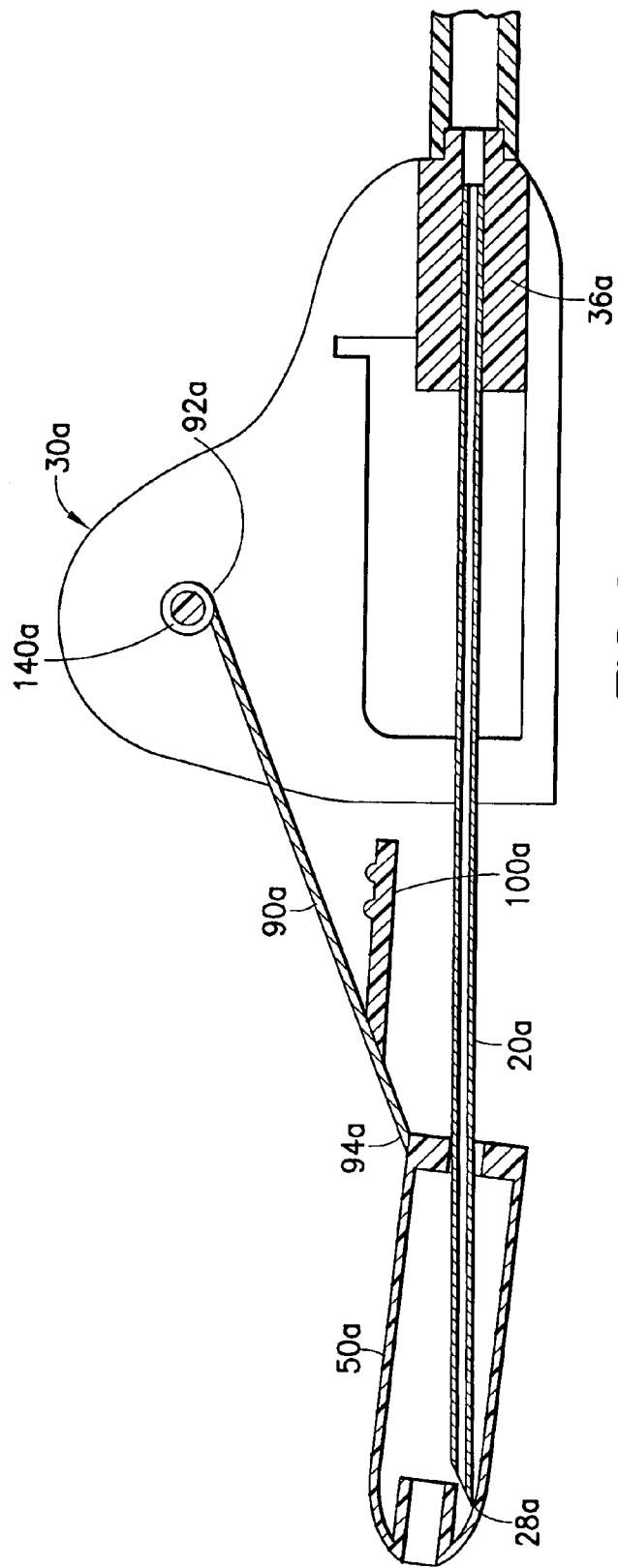
FIG. 6 is a side cross-sectional view of the alternate shieldable needle device of FIG. 5 with the needle device in a fully shielded state.

In the alternate embodiment of FIGS. 5 and 6, needle device 12a works in a similar manner as the device described in connection with the embodiment of FIGS. 1-4, with the exception that drive mechanism 90a is coiled as a wound spring as opposed to being bent around a bend as a leaf spring. For example, as shown in FIG. 5, when tip guard assembly 50a is in a retracted position with puncture tip 28a of needle cannula 20a exposed, first end 92a is connected to connector 44a with drive mechanism 90a wound about connector 44a, thereby creating energy within drive mechanism 90a for establishing a biasing force against tip guard assembly 50a attached at second end 94a. When release latch 100a is released, drive mechanism 90a unwinds and becomes uncoiled, thereby releasing it's energy and forcing tip guard assembly 50a to a shielding or extended position about puncture tip 28a. In such an embodiment, only a single point of connection is desirably provided between the first and second lateral extensions of housing 30a, such as at connector 44a. Moreover, a bushing 140a is desirably provided about connector 44a, as a point of attachment between drive mechanism 90a and housing 30a, with bushing 140a permitting unwinding of drive mechanism 90a around connector 44a.

Figure 7:
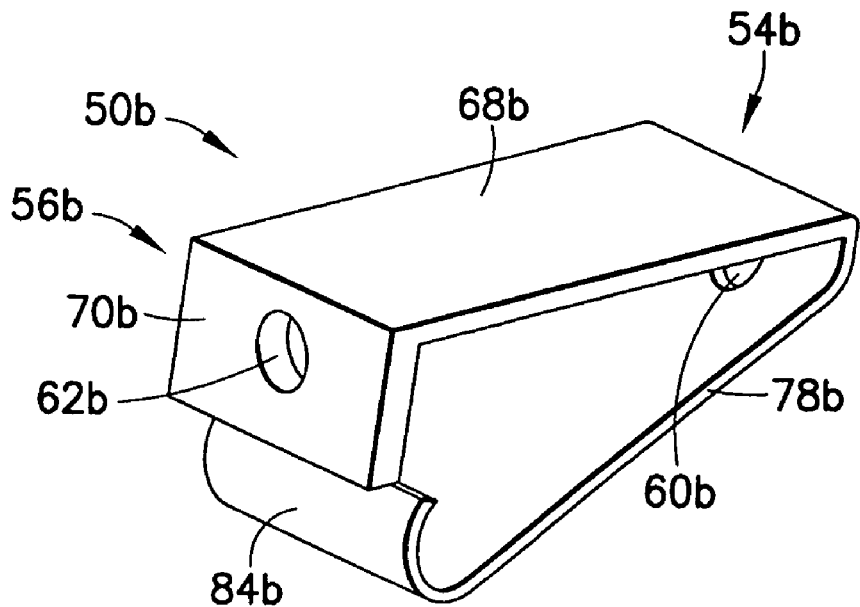
FIG. 7 is a perspective view of a tip guard for use in an alternate embodiment of the present invention.
Figure 8:
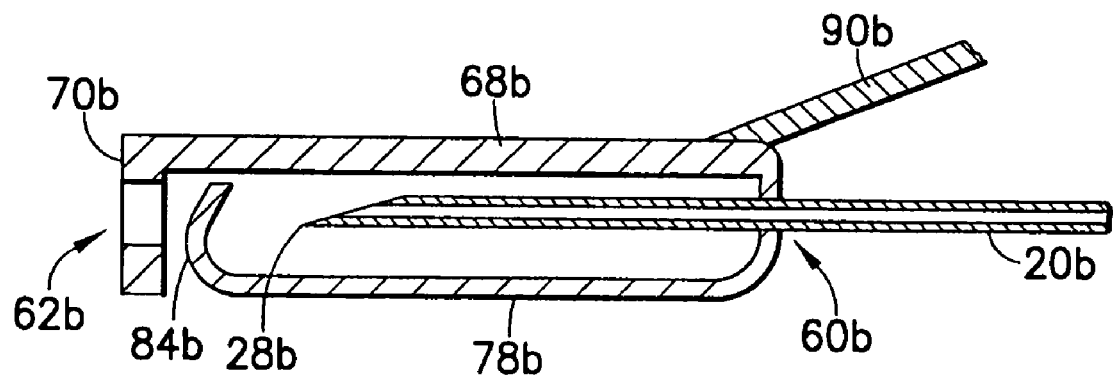
FIG. 8 is an enlarged cross-sectional view of the alternate tip guard of FIG. 7 shown extended over the puncture tip of the needle cannula.

In the alternate embodiment of FIGS. 7 and 8, tip guard assembly 50b is provided as a one-piece assembly including a rearward or proximal end 54b and a forward or distal end 56b, with top extent 68b defining the top portion of tip guard assembly 50b for extending longitudinally along a portion of the needle cannula between proximal end 54b and distal end 56b. Top extent 68b bends downwardly at distal end 56b to form front end wall 70b. At proximal end 54b, top extent 68b bends backward to form spring leg 78b which extends back toward the distal end 56b of tip guard assembly 50b, with lockout leg 84b bending upward and backward to form an end wall, as seen in FIG. 7. Proximal end 54b of tip guard assembly 50b includes proximal opening 60b, while distal end 56b of tip guard assembly 50b includes distal opening 62b extending through front end wall 70b. Proximal opening 60b and distal opening 62b are provided for accommodating the needle cannula extending therethrough. The bends in lockout leg 84b enable secure protective engagement with puncture tip 28b of the needle cannula and further enable smooth axial sliding movement of tip guard assembly 50b along the needle cannula.

Figure 9:
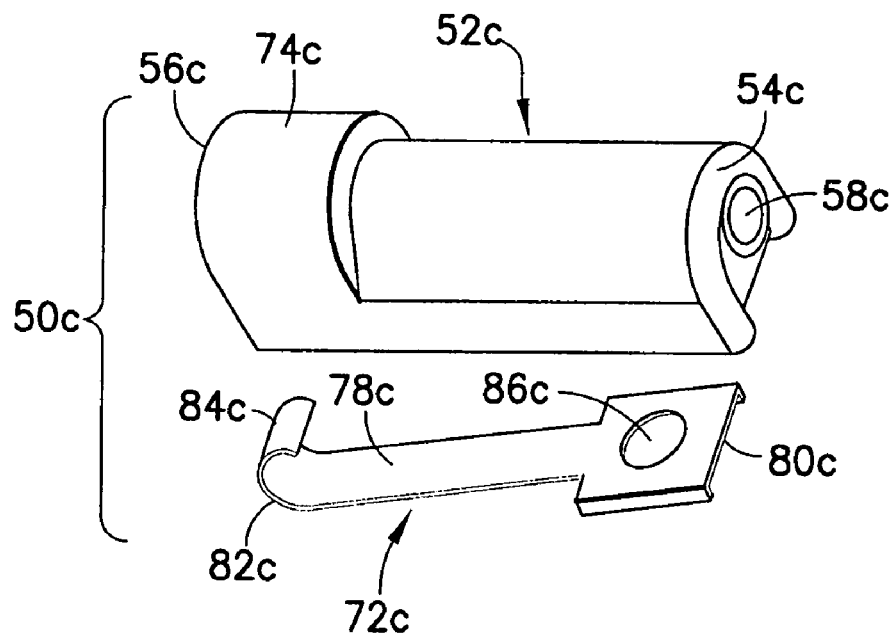
FIG. 9 is a perspective view of an additional tip guard for use in a further embodiment of the present invention.
Figure 10:
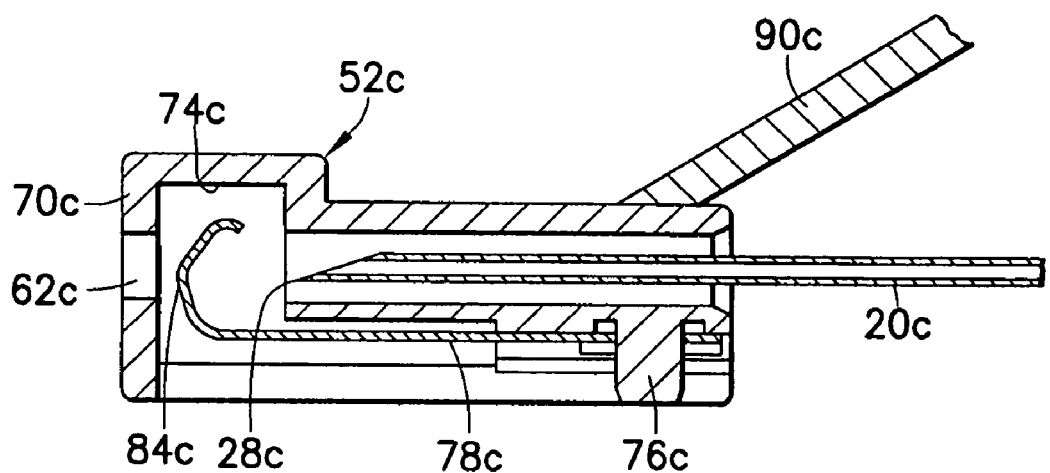
FIG. 10 is an enlarged cross-sectional view of the alternate tip guard of FIG. 10 shown extended over the puncture tip of the needle cannula.

FIGS. 9 and 10 depict a further tip guard assembly 50c for use in connection with the present invention, in the form of a two-piece assembly. In the two-piece assembly of FIGS. 9 and 10, tip guard assembly 50c includes housing 52c having a proximal end 54c and a distal end 56c, with a portion of internal passage 58c adjacent distal end 56c defining an enlarged clip receptacle 74c. A clip mounting post 76c extends downwardly from housing 52c at a location near proximal end 54c of housing 52c.

A clip 72c is unitarily stamped and formed from a resiliently deflectable metallic material. Clip 72c includes a planar spring leg 78c with a proximal end 80c and an opposed distal end 82c. A mounting aperture 86c extends through spring leg 78c at a location near proximal end 80c. The mounting aperture has a diameter approximately equal to or slightly less than the diameter of mounting post 76c of housing 52c. As such, mounting post 76c can be forced through the mounting aperture when the axis of mounting post 76c and the axis of mounting aperture 86c are substantially co-linear. A lockout leg 84c extends angularly from distal end 82c of spring leg 78c. Lockout leg 84c is bent back toward proximal end 80c of clip 72c. The bends in lockout leg 84c enable secure protective engagement with puncture tip 28c of needle cannula 20c and further enable smooth axial sliding movement of tip guard assembly 50c along needle cannula 20c.

While the needle assembly of the present invention has been described in terms of an embodiment for use in connection with a blood collection system, it is further contemplated that the needle assembly could be used with other medical procedures, such as in conjunction with a conventional intravenous infusion set, a hypodermic needle assembly, or a double ended needle assembly for blood collection, all of which are well-known in the art for use with needle devices.

Figure 11:
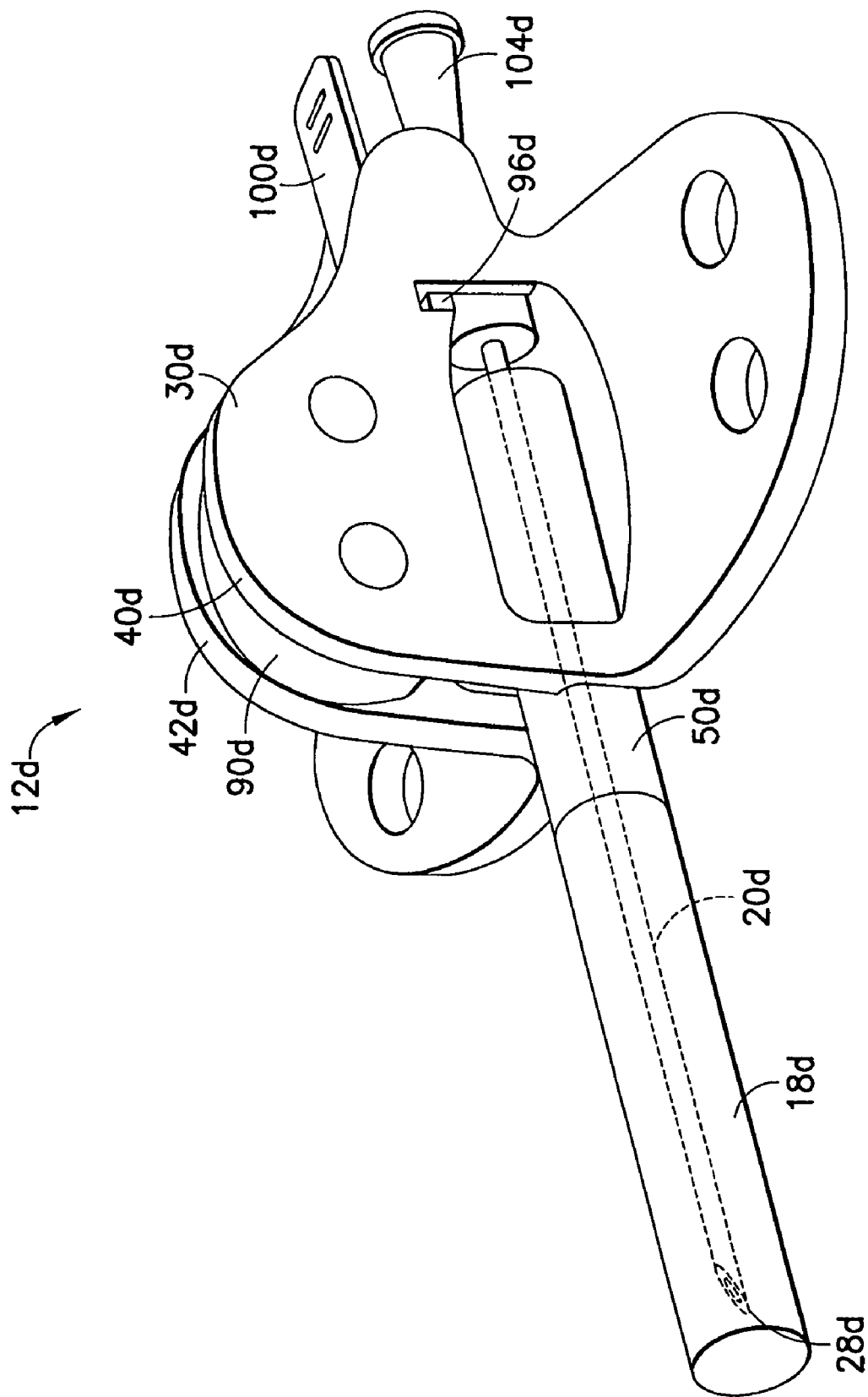
FIG. 11 is a perspective view of a needle device in accordance with a further embodiment of the present invention.
Figure 12:
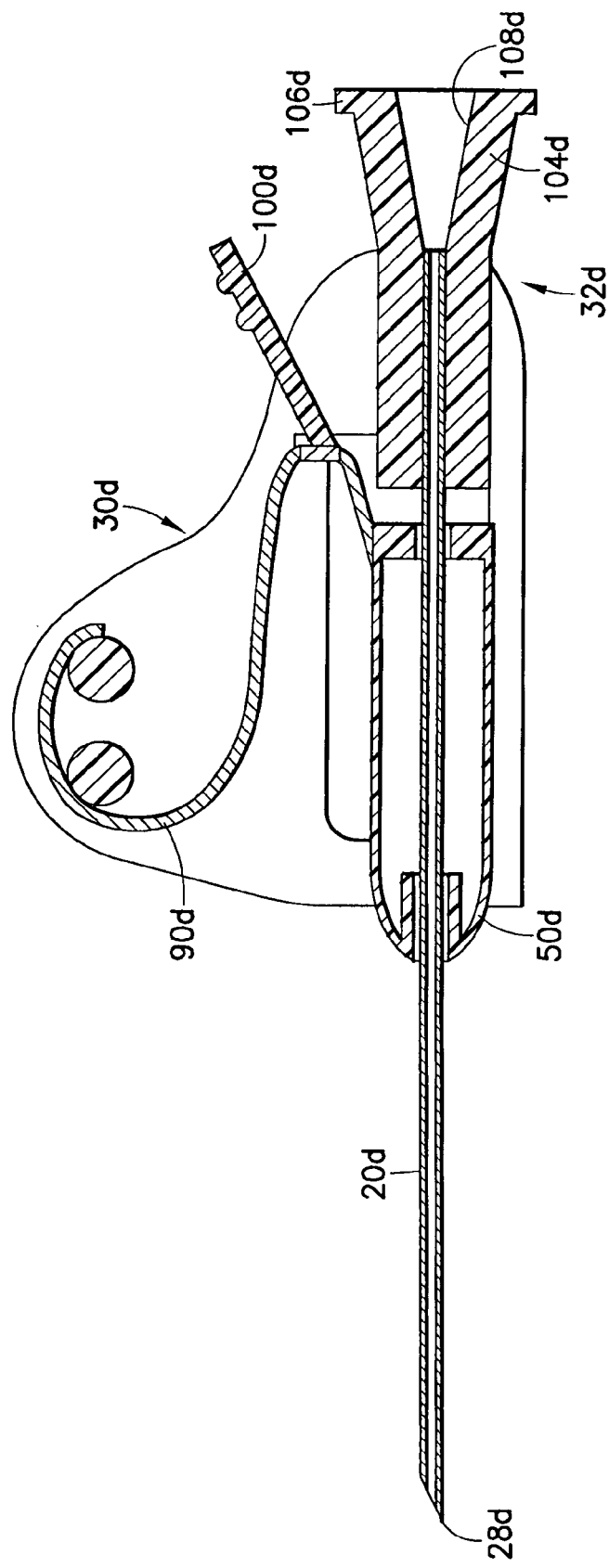
FIG. 12 is a side cross-sectional view of the needle device in FIG. 11.

For example, FIGS. 11 and 12 depict safety needle device 12d for attachment to conventional medical devices, such as conventional needle holders for blood collection, syringes, and the like. As shown in FIGS. 1-4, the safety needle device 12 includes a needle cannula 20, a housing 30, and a tip guard assembly 50, as set forth in the embodiment described above. In the embodiment of FIGS. 11 and 12, the safety needle device 12d is an independent component for attachment to a medical device, such as a hypodermic syringe. As such, housing 30d acts as a base housing for providing such attachment.

Accordingly, housing 30d includes means for attachment with a medical device, such as a hypodermic syringe, at proximal end 32d. For example, housing 30d may include a threaded end at the proximal end 32d thereof. Desirably, as shown in FIGS. 11 and 12, housing 30d includes a female luer fitting 104d and a luer flange 106d at the proximal end thereof. Female luer fitting 104d includes an inner tapered surface 108d. Such an arrangement provides for attachment with a luer collar, such as a syringe luer collar. Such a luer fitting enables safety needle device 12d to be sold as a sterile needle device for use with a conventional medical device adapted for use with a luer fitting. Since the safety needle device 12d of FIGS. 11 and 12 is intended for use with a syringe or the like, first and second lateral wings 130 and 132, such as those shown in FIGS. 1 and 2, are not necessarily provided.

Figure 13:
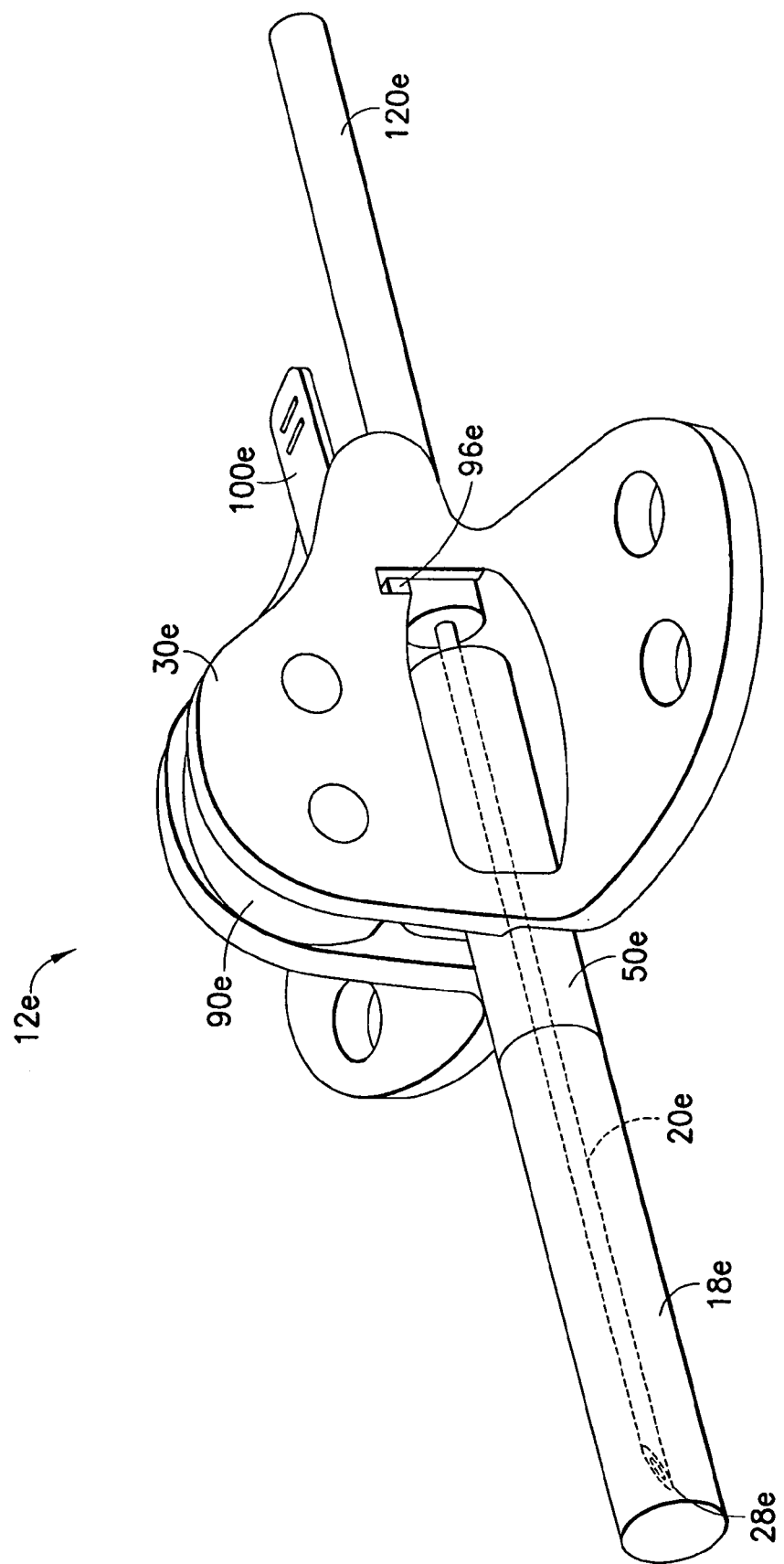
FIG. 13 is a perspective view of a needle device in accordance with yet a further embodiment.
Figure 14:
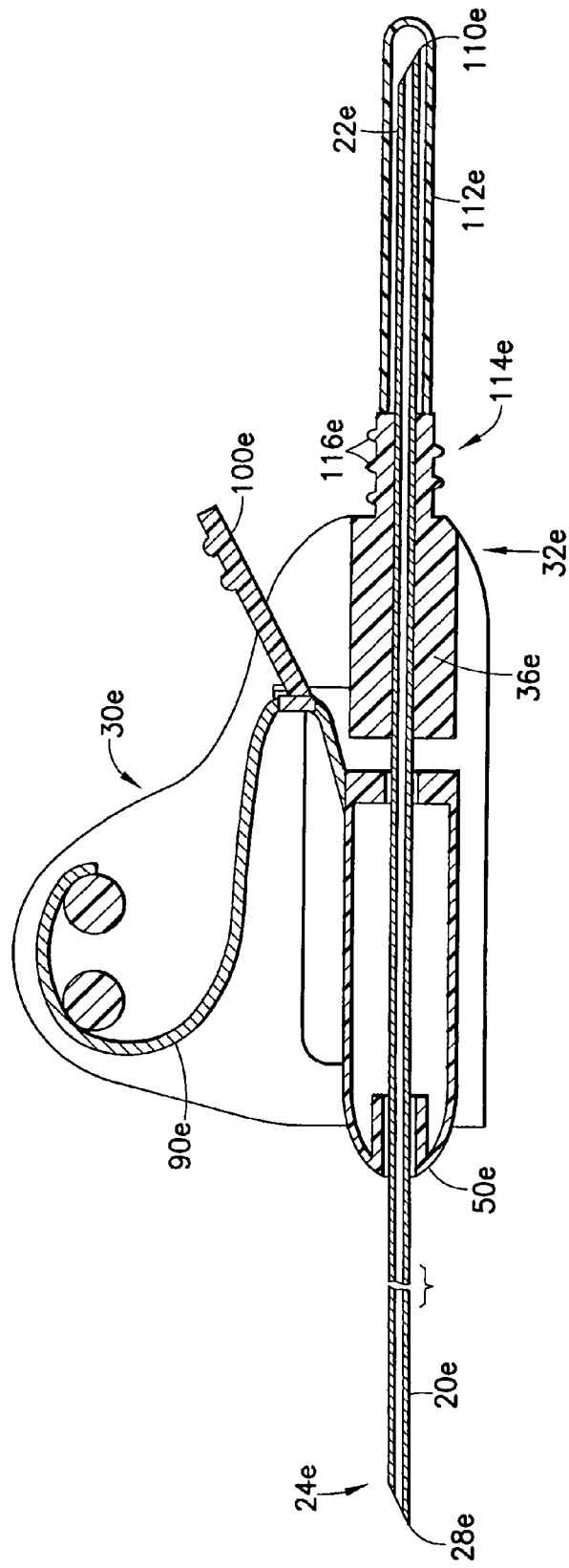
FIG. 14 is a side cross-sectional view of the needle device of FIG. 13.

In a further embodiment depicted in FIGS. 13 and 14, safety needle device 12e is provided as an independent component in the form of a double-ended needle assembly for attachment to a needle holder, as is known for use in connection with blood sampling procedures. In the needle device 12e depicted in FIGS. 13 and 14, needle cannula 20e is in the form of double-ended needle, including puncture tip 28e as an intravenous puncture tip at distal end 24e thereof, and a non-patient puncture tip 110e at proximal end 22e thereof. Needle cannula 20e extends through hub 36e of housing 30e. Proximal end 22e of needle cannula 20e desirably includes an elastomeric sleeve 112e covering non-patient puncture tip 110e.

Housing 30e desirably includes means for attachment to a separate needle holder (not shown). For example, housing 30e may include a threaded end 114e at the proximal end 32e thereof. Preferably, threaded end 114e comprises male threads 116e for mounting needle device 12e on a standard needle holder. As needle device 12e is provided as an independent component for attachment to a separate needle holder, needle device 12e is desirably packaged as shown in FIG. 13, including packaging cover 18e covering distal end 24e of needle cannula 20e, and further including a second packaging cover 120e covering proximal end 22e of needle cannula 20e.

While the present invention is satisfied by embodiments in many different forms, there is shown in the drawings and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

What is claimed is:

1. A shieldable needle device comprising:
   a housing including a first lateral extension and a second lateral extension, said first lateral extension and said second lateral extension interconnected at a rearward end of said housing forming a hub portion with said first lateral extension and said second lateral extension being fixed with respect to the hub portion;
   a needle cannula including a forward end and a rearward end, said needle cannula extending from said hub portion of said housing;
   a tip guard axially movable along said needle cannula between a retracted position where said forward end of said needle cannula is exposed and an extended position where said tip guard protectively surrounds said forward end of said needle cannula; and
   a flexibly resilient drive mechanism for biasing said tip guard to said extended position including a first end anchored to said housing between said first lateral extension and said second lateral extension, and a second end anchored to said tip guard, said drive mechanism capable of being retained in a biased state between said first lateral extension and said second lateral extension when said tip guard is in said retracted position.

2. A shieldable needle device as in claim 1, wherein said drive mechanism includes an axis of rotation perpendicular to said needle.

3. A shieldable needle device as in claim 1, wherein said drive mechanism comprises a coiled spring wound between said first lateral extension and said second lateral extension.

4. A shieldable needle device as in claim 1, wherein said drive mechanism includes a locking lug adjacent said second end thereof, said locking lug capable of frictional engagement with said housing for retaining said drive mechanism in a biased state between said first lateral extension and said second lateral extension when said tip guard is in said retracted position.

5. A shieldable needle device as in claim 4, further comprising a release latch for releasing said locking lug from frictional engagement with said housing, thereby causing said drive mechanism to bias said tip guard to said extended position.

6. A shieldable needle device as in claim 5, wherein said release latch includes a surface having a profile for accommodating a user's finger.

7. A shieldable needle device as in claim 1, wherein said first lateral extension of said housing includes a first lateral wing and said second lateral extension of said housing includes a second lateral wing, said first lateral wing and said second lateral wing forming a pair of generally planar wings extending from opposing sides of said housing.

8. A shieldable needle device as in claim 1, wherein said housing is adapted for connection to a blood collection set.

9. A shieldable needle device as in claim 1, wherein said housing further includes a connector adapted for attachment with a hypodermic syringe.

10. A shieldable needle device as in claim 1, including a packaging cover extending over said needle cannula.

11. A shieldable needle device comprising:
    a housing including a first lateral extension and a second lateral extension, said first lateral extension and said second lateral extension interconnected at a rearward end of said housing forming a hub portion;
    a needle cannula including a forward end and a rearward end, said needle cannula extending from said hub portion of said housing;
    a tip guard axially movable along said needle cannula between a retracted position where said forward end of said needle cannula is exposed and an extended position where said tip guard protectively surrounds said forward end of said needle cannula; and
    a flexibly resilient drive mechanism for biasing said tip guard to said extended position including a first end anchored to said housing between said first lateral extension and said second lateral extension, and a second end anchored to said tip guard, said drive mechanism capable of being retained in a biased state between said first lateral extension and said second lateral extension when said tip guard is in said retracted position;
    wherein said drive mechanism comprises a leaf spring.

12. A shieldable needle wingset for blood collection comprising:
- a fixture for connecting the wingset to a receptacle;
- a flexible tube having opposed first and second ends, said first end of said flexible tube being connected to said fixture;
- a wingset housing mounted to said second end of said flexible tube, said wingset housing including a first lateral section having a first lateral wing and a first dorsal fin, and a second lateral section having a second lateral wing and a second dorsal fin, said first lateral section and said second lateral section interconnected at a rearward end of said wingset housing forming a hub portion;
- a needle cannula including a forward end and a rearward end, said needle cannula extending from said hub portion of said wingset housing;
- a tip guard axially movable along said needle cannula between a retracted position where said forward end of said needle cannula is exposed and an extended position where said tip guard protectively surrounds said forward end of said needle cannula; and
- a leaf spring for biasing said tip guard to said extended position including a first end anchored to said wingset housing between said first dorsal fin and said second dorsal fin, and a second end anchored to said tip guard, said leaf spring capable of being retained in a biased state between said first dorsal fin and said second dorsal fin when said tip guard is in said retracted position.

13. A shieldable needle wingset as in claim 12, wherein said leaf spring is wound into a coiled spring about a bar extending between said first lateral extension and said second lateral extension.

14. A shieldable needle wingset as in claim 12, wherein said leaf spring includes a locking lug adjacent said second end thereof, said locking lug capable of frictional engagement with said housing for retaining said leaf spring in a biased state between said first dorsal fin and said second dorsal fin when said tip guard is in said retracted position.

15. A shieldable needle wingset as in claim 14, further comprising a release latch for releasing said locking lug from frictional engagement with said housing, thereby causing said leaf spring to bias said tip guard to said extended position.

16. A shieldable needle wingset as in claim 15, wherein said release latch includes a surface having a profile for accommodating a user's finger.

17. A shieldable needle device comprising:
- a housing including a first lateral extension and a second lateral extension, said first lateral extension and said second lateral extension interconnected at a rearward end of said housing forming a hub portion;
- a needle cannula including a forward end and a rearward end, said needle cannula extending from said hub portion of said housing;
- a tip guard axially movable along said needle cannula between a retracted position where said forward end of said needle cannula is exposed and an extended position where said tip guard protectively surrounds said forward end of said needle cannula;
- a flexibly resilient drive mechanism for biasing said tip guard to said extended position including a first end anchored to said housing between said first lateral extension and said second lateral extension, and a second end anchored to said tip guard, said drive mechanism capable of being retained in a biased state between said first lateral extension and said second lateral extension when said tip guard is in said retracted position;
- wherein said drive mechanism includes a locking lug adjacent said second end thereof, said locking lug capable of frictional engagement with said housing for retaining said drive mechanism in a biased state between said first lateral extension and said second lateral extension when said tip guard is in said retracted position; and a release latch for releasing said locking lug from frictional engagement with said housing, thereby causing said drive mechanism to bias said tip guard to said extended position;
- wherein said release latch extends from said tip guard, and said drive mechanism is attached to said release latch at said locking lug.

18. A shieldable needle device comprising:
- a housing including a first lateral extension and a second lateral extension, said first lateral extension and said second lateral extension interconnected at a rearward end of said housing forming a hub portion with said first lateral extension and said second lateral extension being fixed with respect to the hub portion;
- a needle cannula including a forward end and a rearward end, said needle cannula extending from said hub portion of said housing;
- a tip guard axially movable along said needle cannula between a retracted position where said forward end of said needle cannula is exposed and an extended position where said tip guard protectively surrounds said forward end of said needle cannula; and
- a drive mechanism interconnecting said housing and said tip guard, with at least a portion of said drive mechanism positioned between said first lateral extension and said second lateral extension, said drive mechanism capable of being retained in a biased state between said first lateral extension and said second lateral extension when said tip guard is in said retracted position.

19. A shieldable needle device comprising:
- a housing comprising a hub portion, a dorsal structure extending radially outward therefrom and at least one laterally extending wing;
- a needle cannula including a forward end and a rearward end, said needle cannula extending from said hub portion of said housing;
- a tip guard axially movable between a retracted position where said forward end of said needle cannula is exposed and an extended position where said tip guard protectively surrounds said forward end of said needle cannula; and
- a drive mechanism interconnecting the housing and the tip guard, said drive mechanism positioned within said dorsal structure of said housing and adapted to be retained therein in a biased state when said tip guard is in the retracted position.

20. A shieldable needle device as in claim 19, wherein the housing comprises a hub portion having first and second lateral extensions extending therefrom, said first and second lateral extensions forming first and second lateral extending wings and first and second dorsal extensions, said first and second dorsal extensions positioned adjacent each other.

* * * * *